United States Patent
Ledbetter et al.

(10) Patent No.: US 12,007,454 B2
(45) Date of Patent: Jun. 11, 2024

(54) DEVICES, SYSTEMS, AND METHODS FOR SUPPRESSING OPTICAL NOISE IN OPTICALLY PUMPED MAGNETOMETERS

(71) Applicant: HI LLC, Los Angeles, CA (US)

(72) Inventors: Micah Ledbetter, Sunnyvale, CA (US); Ricardo Jimenez-Martinez, Culver City, CA (US); Geoffrey Iwata, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 80 days.

(21) Appl. No.: 17/689,669

(22) Filed: Mar. 8, 2022

(65) Prior Publication Data

US 2022/0299584 A1     Sep. 22, 2022

Related U.S. Application Data

(60) Provisional application No. 63/224,768, filed on Jul. 22, 2021, provisional application No. 63/159,823, filed on Mar. 11, 2021.

(51) Int. Cl.
*G01V 3/00* (2006.01)
*A61B 5/245* (2021.01)
*G01R 33/26* (2006.01)

(52) U.S. Cl.
CPC ............. *G01R 33/26* (2013.01); *A61B 5/245* (2021.01)

(58) Field of Classification Search
CPC ............. G01R 33/3415; G01R 33/543; G01R 33/5659; G01R 33/36; A61B 5/055
(Continued)

(56) References Cited

U.S. PATENT DOCUMENTS

| 3,173,082 A | 3/1965 | Bell et al. |
| 3,257,608 A | 6/1966 | Bell et al. |

(Continued)

FOREIGN PATENT DOCUMENTS

| CN | 104730484 | 6/2015 |
| CN | 107562188 | 1/2018 |

(Continued)

OTHER PUBLICATIONS

Allred, J. C., Lyman, R. N., Kornack, T. W., & Romalis, M. V. (2002). High-sensitivity atomic magnetometer unaffected by spin-exchange relaxation. Physical review letters, 89(13), 130801.

(Continued)

*Primary Examiner* — Walter L Lindsay, Jr.
*Assistant Examiner* — Frederick Wenderoth
(74) *Attorney, Agent, or Firm* — Branch Partners PLLC; Bruce E. Black

(57) ABSTRACT

A magnetic field measurement system includes a light source that emits a light beam; an optical fiber to transmit the light beam; a variable optical attenuator to increase stability of an intensity of the light beam; a beam splitter to divide the light beam into an OPM light beam and a monitor light beam; a monitor detector to detect the monitor light beam and generate a monitor signal; a vapor cell with alkali metal atoms disposed therein and configured for transmission of the OPM light beam through the vapor cell; an OPM detector to detect the OPM light beam after transmission through the vapor cell and generate an OPM signal; and a group delay filter to combine the monitor signal and the OPM signal to generate a reduced noise OPM signal, where the group delay filter accounts for a phase difference between the monitor signal and the OPM signal.

20 Claims, 5 Drawing Sheets

(58) Field of Classification Search
USPC .......................................................... 324/304
See application file for complete search history.

(56) References Cited

U.S. PATENT DOCUMENTS

| | | | |
|---|---|---|---|
| 3,495,161 A | 2/1970 | Bell | |
| 3,501,689 A | 3/1970 | Robbiano | |
| 3,513,381 A | 5/1970 | Happer, Jr. | |
| 4,193,029 A | 3/1980 | Cioccio et al. | |
| 4,951,674 A | 8/1990 | Zanakis et al. | |
| 5,189,368 A | 2/1993 | Chase | |
| 5,192,921 A | 3/1993 | Chantry et al. | |
| 5,225,778 A | 7/1993 | Chaillout et al. | |
| 5,254,947 A | 10/1993 | Chaillout et al. | |
| 5,309,095 A | 5/1994 | Ahonen et al. | |
| 5,442,289 A | 8/1995 | Dilorio et al. | |
| 5,444,372 A | 8/1995 | Wikswo, Jr. et al. | |
| 5,471,985 A | 12/1995 | Warden | |
| 5,506,200 A | 4/1996 | Hirschkoff et al. | |
| 5,526,811 A | 6/1996 | Lypchuk | |
| 5,713,354 A | 2/1998 | Warden | |
| 6,144,872 A | 11/2000 | Graetz | |
| 6,339,328 B1 | 1/2002 | Keene et al. | |
| 6,472,869 B1 | 10/2002 | Upschulte et al. | |
| 6,665,553 B2 | 12/2003 | Kandori et al. | |
| 6,806,784 B2 | 10/2004 | Hollberg et al. | |
| 6,831,522 B2 | 12/2004 | Kitching et al. | |
| 7,038,450 B2 | 5/2006 | Romalis et al. | |
| 7,102,451 B2 | 9/2006 | Happer et al. | |
| 7,145,333 B2 | 12/2006 | Romalis et al. | |
| 7,521,928 B2 | 4/2009 | Romalis et al. | |
| 7,656,154 B2 | 2/2010 | Kawabata et al. | |
| 7,826,065 B1 | 11/2010 | Okandan et al. | |
| 7,872,473 B2 | 1/2011 | Kitching et al. | |
| 7,994,783 B2 | 8/2011 | Ledbetter et al. | |
| 8,054,074 B2 | 11/2011 | Ichihara et al. | |
| 8,212,556 B1 | 7/2012 | Schwindt et al. | |
| 8,258,884 B2 | 9/2012 | Borwick, III et al. | |
| 8,319,156 B2 | 11/2012 | Borwick, III et al. | |
| 8,334,690 B2 | 12/2012 | Kitching et al. | |
| 8,373,413 B2 | 2/2013 | Sugioka | |
| 8,405,389 B2 | 3/2013 | Sugioka et al. | |
| 8,587,304 B2 | 11/2013 | Budker et al. | |
| 8,836,327 B2 | 9/2014 | French et al. | |
| 8,906,470 B2 | 12/2014 | Overstolz et al. | |
| 8,941,377 B2 | 1/2015 | Mizutani et al. | |
| 9,084,549 B2 | 7/2015 | Desain et al. | |
| 9,095,266 B1 | 8/2015 | Fu | |
| 9,116,201 B2 | 8/2015 | Shah et al. | |
| 9,140,590 B2 | 9/2015 | Waters et al. | |
| 9,140,657 B2 | 9/2015 | Ledbetter et al. | |
| 9,169,974 B2 | 10/2015 | Parsa et al. | |
| 9,244,137 B2 | 1/2016 | Kobayashi et al. | |
| 9,291,508 B1 | 3/2016 | Biedermann et al. | |
| 9,343,447 B2 | 3/2016 | Parsa et al. | |
| 9,366,735 B2 | 6/2016 | Kawabata et al. | |
| 9,383,419 B2 | 7/2016 | Mizutani et al. | |
| 9,395,425 B2 | 7/2016 | Diamond et al. | |
| 9,417,293 B2 | 8/2016 | Schaffer et al. | |
| 9,429,918 B2 | 8/2016 | Parsa et al. | |
| 9,568,565 B2 | 2/2017 | Parsa et al. | |
| 9,575,144 B2 | 2/2017 | Kornack et al. | |
| 9,601,225 B2 | 3/2017 | Parsa et al. | |
| 9,638,768 B2 | 5/2017 | Foley et al. | |
| 9,639,062 B2 | 5/2017 | Dyer et al. | |
| 9,677,905 B2 | 6/2017 | Waters et al. | |
| 9,726,626 B2 | 8/2017 | Smith et al. | |
| 9,726,733 B2 | 8/2017 | Smith et al. | |
| 9,791,536 B1 | 10/2017 | Alem et al. | |
| 9,829,544 B2 | 11/2017 | Bulatowicz | |
| 9,846,054 B2 | 12/2017 | Waters et al. | |
| 9,851,418 B2 | 12/2017 | Wolf et al. | |
| 9,869,731 B1 | 1/2018 | Hovde et al. | |
| 9,915,711 B2 | 3/2018 | Kornack et al. | |
| 9,927,501 B2 | 3/2018 | Kim et al. | |
| 9,948,314 B2 | 4/2018 | Dyer et al. | |
| 9,964,609 B2 | 5/2018 | Ichihara et al. | |
| 9,964,610 B2 | 5/2018 | Shah et al. | |
| 9,970,999 B2 | 5/2018 | Larsen et al. | |
| 9,995,800 B1 | 6/2018 | Schwindt et al. | |
| 10,024,929 B2 | 7/2018 | Parsa et al. | |
| 10,088,535 B1 | 10/2018 | Shah | |
| 10,162,016 B2 | 12/2018 | Gabrys et al. | |
| 10,194,865 B2 | 2/2019 | Le et al. | |
| 10,314,508 B2 | 6/2019 | Desain et al. | |
| 10,371,764 B2 | 8/2019 | Morales et al. | |
| 10,772,561 B2 | 9/2020 | Donaldson | |
| 2004/0232912 A1 | 11/2004 | Tsukamoto et al. | |
| 2005/0007118 A1 | 1/2005 | Kitching et al. | |
| 2005/0046851 A1 | 3/2005 | Riley et al. | |
| 2005/0062532 A1* | 3/2005 | Gurvich | H03F 3/189 330/151 |
| 2005/0206377 A1 | 9/2005 | Romalis et al. | |
| 2007/0120563 A1 | 5/2007 | Kawabata et al. | |
| 2007/0167723 A1 | 7/2007 | Park et al. | |
| 2007/0205767 A1 | 9/2007 | Xu et al. | |
| 2009/0001979 A1* | 1/2009 | Kawabata | G01R 33/26 324/244.1 |
| 2009/0079426 A1 | 3/2009 | Anderson | |
| 2009/0091819 A1* | 4/2009 | Bolshtyansky | H01S 3/1301 359/341.5 |
| 2009/0101806 A1 | 4/2009 | Masuda | |
| 2009/0212769 A1* | 8/2009 | Stoica | G01R 33/032 324/244.1 |
| 2010/0219820 A1 | 9/2010 | Skidmore et al. | |
| 2011/0062956 A1 | 3/2011 | Edelstein et al. | |
| 2012/0112749 A1 | 5/2012 | Budker et al. | |
| 2013/0082700 A1 | 4/2013 | Mizutani et al. | |
| 2013/0082701 A1 | 4/2013 | Mizutani et al. | |
| 2013/0265042 A1* | 10/2013 | Kawabata | G01R 33/26 324/301 |
| 2014/0121491 A1 | 5/2014 | Zhang | |
| 2014/0306700 A1 | 10/2014 | Kamada et al. | |
| 2014/0330404 A1* | 11/2014 | Abdelghani | A61B 5/4851 700/83 |
| 2014/0354275 A1 | 12/2014 | Sheng et al. | |
| 2015/0022200 A1 | 1/2015 | Ichihara et al. | |
| 2015/0054504 A1 | 2/2015 | Ichihara et al. | |
| 2015/0378316 A1 | 12/2015 | Parsa et al. | |
| 2016/0061913 A1 | 3/2016 | Kobayashi et al. | |
| 2016/0116553 A1 | 4/2016 | Kim et al. | |
| 2016/0223627 A1 | 8/2016 | Shah et al. | |
| 2016/0291099 A1 | 10/2016 | Ueno | |
| 2016/0313417 A1 | 10/2016 | Kawabata et al. | |
| 2017/0023653 A1 | 1/2017 | Kobayashi et al. | |
| 2017/0023654 A1 | 1/2017 | Kobayashi et al. | |
| 2017/0067969 A1 | 3/2017 | Butters et al. | |
| 2017/0199138 A1 | 7/2017 | Parsa et al. | |
| 2017/0261564 A1 | 9/2017 | Gabrys et al. | |
| 2017/0307757 A1* | 10/2017 | Hinderling | G01S 7/4817 |
| 2017/0331485 A1 | 11/2017 | Gobet et al. | |
| 2017/0343617 A1 | 11/2017 | Manickam et al. | |
| 2017/0343695 A1 | 11/2017 | Stetson et al. | |
| 2017/0356969 A1 | 12/2017 | Ueno | |
| 2017/0360322 A1 | 12/2017 | Ueno | |
| 2017/0363695 A1 | 12/2017 | Ueno | |
| 2018/0003777 A1 | 1/2018 | Sorenson et al. | |
| 2018/0038921 A1 | 2/2018 | Parsa et al. | |
| 2018/0100749 A1 | 4/2018 | Waters et al. | |
| 2018/0128885 A1 | 5/2018 | Parsa et al. | |
| 2018/0156875 A1 | 6/2018 | Herbsommer et al. | |
| 2018/0210039 A1* | 7/2018 | Shalev | G01V 3/081 |
| 2018/0219353 A1 | 8/2018 | Shah | |
| 2018/0238974 A1* | 8/2018 | Shah | G01R 33/323 |
| 2018/0313908 A1 | 11/2018 | Knappe et al. | |
| 2018/0313913 A1 | 11/2018 | DeNatale et al. | |
| 2018/0372813 A1 | 12/2018 | Bulatowicz et al. | |
| 2019/0391213 A1 | 12/2019 | Alford | |
| 2020/0025844 A1 | 1/2020 | Alford et al. | |
| 2020/0056263 A1 | 2/2020 | Bhattacharyya et al. | |
| 2020/0057115 A1 | 2/2020 | Jiménez-Martínez et al. | |
| 2020/0057116 A1 | 2/2020 | Zorzos et al. | |
| 2020/0064421 A1 | 2/2020 | Kobayashi et al. | |
| 2020/0072916 A1 | 3/2020 | Alford et al. | |

(56) References Cited

U.S. PATENT DOCUMENTS

| | | | |
|---|---|---|---|
| 2020/0088811 | A1 | 3/2020 | Mohseni |
| 2020/0109481 | A1 | 4/2020 | Sobek et al. |
| 2020/0123416 | A1 | 4/2020 | Bhattacharyya et al. |
| 2020/0191883 | A1 | 6/2020 | Bhattacharyya et al. |
| 2020/0241094 | A1 | 7/2020 | Alford |
| 2020/0256929 | A1 | 8/2020 | Ledbetter et al. |
| 2020/0309873 | A1 | 10/2020 | Ledbetter et al. |
| 2020/0334559 | A1 | 10/2020 | Anderson et al. |
| 2020/0341081 | A1 | 10/2020 | Mohseni et al. |
| 2020/0381128 | A1 | 12/2020 | Pratt et al. |
| 2020/0400763 | A1 | 12/2020 | Pratt |
| 2021/0011094 | A1 | 1/2021 | Bednarke |
| 2021/0015385 | A1 | 1/2021 | Katnani et al. |
| 2021/0015427 | A1 | 1/2021 | Shah et al. |
| 2021/0041512 | A1 | 2/2021 | Pratt et al. |
| 2021/0041513 | A1 | 2/2021 | Mohseni |
| 2021/0063510 | A1 | 3/2021 | Ledbetter |

FOREIGN PATENT DOCUMENTS

| | | | | |
|---|---|---|---|---|
| CN | 110244242 | A | * 9/2019 | |
| CN | 110350982 | A | * 10/2019 | ........... H04B 10/541 |
| CN | 110742607 | | 2/2020 | |
| CN | 110859610 | | 3/2020 | |
| EP | 2447723 | A1 | * 5/2012 | ............. B82Y 20/00 |
| EP | 2738627 | A3 | 6/2014 | |
| EP | 2380029 | B1 | 10/2015 | |
| EP | 3037836 | B1 | 9/2017 | |
| JP | 2016109665 | | 6/2016 | |
| JP | 2018004462 | | 1/2018 | |
| KR | 1893948 | B1 | * 9/2018 | ......... G01B 11/2441 |
| WO | 92/01362 | | 1/1992 | |
| WO | 2005/081794 | | 9/2005 | |
| WO | 2014/031985 | | 2/2014 | |
| WO | 2017/095998 | | 6/2017 | |
| WO | 2020/084194 | | 4/2020 | |

OTHER PUBLICATIONS

Balabas et al. Polarized alkali vapor with minute-long transverse spin-relaxation time, Phys. Rev. Lett. 105, 070801—Published Aug. 12, 2010.
Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.
Dmitry Budker and Michael Romalis, "Optical Magnetometry," Nature Physics, 2008, https://arxiv.org/abs/physics/0611246v1.
Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).
Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.
Donley, E.A. & Hodby, E & Hollberg, L & Kitching, J. (2007). Demonstration of high-performance compact magnetic shields for chip-scale atomic devices. The Review of scientific instruments. 78. Aug. 31, 2002.
Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.
Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10). ISSN 2331-7019.
Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.
Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.
Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.
Kominis, I.K., Kornack, T.W., Allred, J.C. and Romalis, M.V., 2003. A subfemtotesla multichannel atomic magnetometer. Nature, 422(6932), p. 596.
Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.
Lenz, J. and Edelstein, S., 2006. Magnetic sensors and their applications. IEEE Sensors journal, 6(3), pp. 631-649.
Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.
Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.
Sander TH, Preusser J, Mhaskar R, Kitching J, Trahms L, Knappe S. Magnetoencephalography with a chip-scale atomic magnetometer. Biomed Opt Express. 2012;3(5):981-90.
J. Seltzer, S & Romalis, Michael. (2010). High-temperature alkali vapor cells with antirelaxation surface coatings. Journal of Applied Physics. 106. 114905-114905. 10.1063/1.3236649.
Seltzer, S. J., and Romalis, M.V., "Unshielded three-axis vector operation of a spin-exchange-relaxation-free atomic magnetometer." Applied physics letters 85.20 (2004): 4804-4806.
Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.
Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.
Volkmar Schultze et al. An Optically Pumped Magnetometer Working in the Light-Shift Dispersed Mz Mode, Sensors 2017, 17, 561; doi:10.3390/s17030561.
Fang, J. and Qin, J., 2012. In situ triaxial magnetic field compensation for the spin-exchange-relaxation-free atomic magnetometer. Review of Scientific Instruments, 83(10), p. 103104.
Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.
Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.
Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.
Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/ s41598-018-20352-x.

(56) References Cited

OTHER PUBLICATIONS

Kim, Young Jin & Savukov, I. (2016). Ultra-sensitive Magnetic Microscopy with an Optically Pumped Magnetometer. Scientific Reports. 6. 24773. 10.1038/srep24773.
Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.
Orang Alem, Rahul Mhaskar, Ricardo Jimenez-Martinez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).
Slocum et al., Self-Calibrating Vector Magnetometer for Space, https://esto.nasa.gov/conferences/estc-2002/Papers/B3P4(Slocum).pdf.
Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69) 90480-0.
J. A. Neuman, P. Wang, and A. Gallagher, Robust high-temperature sapphire cell for metal vapors, Review of Scientific Instruments, vol. 66, Issue 4, Apr. 1995, pp. 3021-3023.
Borna, Amir, et al. "A 20-channel magnetoencephalography system based on optically pumped magnetometers." Physics in Medicine & Biology 62.23 (2017): 8909.
R. E. Slocum & L. J. Ryan, Design and operation of the minature vector laser magnetometer, Nasa Earth Science Technology Conference 2003.
Schoenmaker, Jeroen & R Pirota, K & Teixeira, Julio. (2013). Magnetic flux amplification by Lenz lenses. The Review of scientific instruments. 84. 085120. 10.1063/1.4819234.
Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically bumped magnetometer. Applied Optics. 56. 5927. 10.1364/AO.56.005927.
Masuda, Y & Ino, T & Skoy, Vadim & Jones, G.L. (2005). 3He polarization via optical pumping in a birefringent cell. Applied Physics Letters. 87. 10.1063/1.2008370.
A.B. Baranga et al., An atomic magnetometer for brain activity imaging, Real Time Conference 2005. 14th IEEE-NPSS. pp. 417-418.
Larry J. Ryan, Robert E. Slocum, and Robert B. Steves, Miniature Vector Laser Magnetometer Measurements of Earth's Field, May 10, 2004, 4 pgs.
Lorenz, V. O., Dai, X., Green, H., Asnicar, T. R., & Cundiff, S. T. (2008). High-density, high-temperature alkali vapor cell. Review of Scientific Instruments, 79(12), 4 pages.
F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.
Huang, Haichao, et al. "Single-beam three-axis atomic magnetometer." Applied Physics Letters 109.6 (2016): 062404. (Year: 2016).
Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.
Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.
Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.
Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.
Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.
Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.
Okada, Y.C., Lahteenmäki, A. and Xu, C., "Experimental analysis of distortion of magnetoencephalography signals by the skull." Clinical neurophysiology 110 (2), 230-238 (1999).
Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors Journal, 19(22), 10163-10175 (2019).
Shah, V., Knappe, S., Schwindt, P.D. and Kitching, J., "Subpicotesla atomic magnetometry with a microfabricated vapour cell." Nature Photon 1, 649-652 (2007).
Griffith, W.C., Knappe, S. and Kitching, J., "Femtotesla atomic magnetometry in a microfabricated vapor cell." Optics express 18, (26), 27167-27172 (2010).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).
Kitching, J., Knappe, S. and Donley, E.A., "Atomic sensors—a review." IEEE Sensors Journal, 11(9), 1749-1758 (2011).
Budker, D. and Romalis, M., "Optical magnetometry". Nature physics, 3(4), 227-234 (2007).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kubler, A., "An MEG-based brain-computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).

(56) References Cited

OTHER PUBLICATIONS

Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Pyragius, T., Marin Florez, H., & Fernholz, T. (2019). A Voigt effect based 3D vector magnetometer. Physical Review A, 100(2), https://doi.org/10.1103/PhysRevA.100.023416.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.
Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.
Stephan Lau et al : "Optimal Magnetic Sensor Vests for Cardiac Source Imaging", Sensors, vol. 16, No. 6, May 24, 2016 (May 24, 2016), p. 754.
Rodriguez Vince: "On the design of door-less access passages to shielded enclosures", 2017 Antenna Measurement Techniques Association Symposium (AMTA), AMTA, Oct. 15, 2017 (Oct. 15, 2017), pp. 1-6.
Orang Alem et al: "Fetal magnetocardiography measurements with an array of microfabricated optically pumped magnetometers", Physics in Medicine and Biology, Institute of Physics Publishing, Bristol GB, vol. 60, No. 12, Jun. 4, 2015 (Jun. 4, 2015), pp. 4797-4811.
Smit Mobile Equipment B.V.: "Mobile MRI", Dec. 19, 2016 (Dec. 19, 2016), Retrieved from the Internet: URL:https://web.archive.org/web/20161219022429/https://smit.one/products/mobile%20mri.html.
Zhang Xin et al.: "Detection and analysis of MEG signals in occipital region with double-channel OPM sensors", Journal of Neuroscience Methods, Elsevier Science Publisher B. V., Amsterdam, NL, vol. 346, Sep. 17, 2020 (Sep. 17, 2020).
Hill RM, Boto E, Holmes N, et al. A tool for functional brain imaging with lifespan compliance [published correction appears in Nat Commun. Dec. 4, 2019;10(1):5628]. Nat Commun. 2019;10(1):4785. Published Nov. 5, 2019. doi:10.1038/s41467-019-12486-x.
Zetter, R., Iivanainen, J. & Parkkonen, L. Optical Co-registration of MRI and On-scalp MEG. Sci Rep 9, 5490 (2019). https://doi.org/10.1038/s41598-019-41763-4.
Garrido-Jurado, Sergio, Rafael Munoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.
Hill RM, Boto E, Rea M, et al. Multi-channel whole-head OPM-MEG: Helmet design and a comparison with a conventional system [published online ahead of print, May 29, 2020]. Neuroimage. 2020;219:116995. doi:10.1016/j.neuroimage.2020.116995.
V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/ CVPR.2014.241.

Holmes, N., Tierney, T.M., Leggett, J et al. Balanced, bi-planar magnetic field and field gradient coils for field compensation in wearable magnetoencephalography. Sci Rep 9, 14196 (2019).
N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.
J. M. Leger et al., In-flight performance of the Absolute Scalar Magnetometer vector mode on board the Swarm satellites, Earth, Planets, and Space (2015) 67:57.
Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.
Gravrand, O., Khokhlov, A., & JL, L. M. (2001). On the calibration of a vectorial 4He pumped magnetometer. Earth, planets and space , 53 (10), 949-958.
Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.
Vrba J, Robinson SE. Signal processing in magnetoencephalography. Methods. 2001;25(2):249-271. doi: 10.1006/ meth.2001.1238.
Uusitalo M and Ilmoniemi R., 1997, Signal-space projection method for separating MEG or EEG into components. Med. Biol. Comput. (35) 135-140.
Taulu S and Kajola M., 2005, Presentation of electromagnetic multichannel data: the signal space separation method. J. Appl. Phys. (97) 124905 (2005).
Taulu S, Simola J and Kajola M., 2005, Applications of the signal space separation method. IEEE Trans. Signal Process. (53) 3359-3372 (2005).
Taulu S, Simola J., 2006, Spatiotemporal signal space separation method for rejecting nearby interference in MEG measurements. Phys. Med. Biol. (51) 1759-1768 (2006).
Johnson, et al., Magnetoencephalography with a two-color pump-probe, fiber-coupled atomic magnetometer, Applied Physics Letters 97, 243703 2010.
Zhang, et al., Magnetoencephalography using a compact multichannel atomic magnetometer with pump-probe configuration, AIP Advances 8, 125028 (2018).
Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.
Ilmoniemi, R. (2009). The triangle phantom in magnetoencephalography. In 24th Annual Meeting of Japan Biomagnetism and Bioelectromagnetics Society, Kanazawa, Japan, 28.29.5.2009 (pp. 6263).
Oyama D. Dry phantom for magnetoencephalography—Configuration, calibration, and contribution. J Neurosci Methods. 2015;251:24-36. doi: 0.1016/j.jneumeth.2015.05.004.
Chutani, R., Maurice, V., Passilly, N et al. Laser light routing in an elongated micromachined vapor cell with diffraction gratings for atomic clock applications. Sci Rep 5, 14001 (2015). https://doi.org/10.1038/srep14001.
Eklund, E. Jesper, Andrei M. Shkel, Svenja Knappe, Elizabeth A. Donley and John Kitching. "Glass-blown spherical microcells for chip-scale atomic devices." (2008).
Jiménez-Martínez R, Kennedy DJ, Rosenbluh M, et al. Optical hyperpolarization and NMR detection of 129Xe on a microfluidic chip. Nat Commun. 2014;5:3908. Published May 20, 2014. doi: 10.1038/ncomms4908.
Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.
Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.
Chella, Federico, Filippo Zappasodi, Laura Marzetti, Stefania Della Penna, and Vittorio Pizzella. "Calibration of a Multichannel MEG

(56) References Cited

OTHER PUBLICATIONS

System Based on the Signal Space Separation Method." Physics in Medicine and Biology 57 (Jul. 13, 2012): 4855-70.

Pasquarelli, A, M De Melis, Laura Marzetti, Hans-Peter Müller, and S N Erné. "Calibration of a Vector-MEG Helmet System." Neurology & Clinical Neurophysiology : NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS One 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

\* cited by examiner

DEVICES, SYSTEMS, AND METHODS FOR SUPPRESSING OPTICAL NOISE IN OPTICALLY PUMPED MAGNETOMETERS

CROSS-REFERENCE TO RELATED APPLICATIONS

This application claims the benefit of U.S. Provisional Patent Application Ser. No. 63/159,823, filed Mar. 11, 2021, and U.S. Provisional Patent Application Ser. No. 63/224,768, filed Jul. 22, 2021, both of which are incorporated herein by reference in their entireties.

FIELD

The present disclosure is directed to magnetic field measurement systems and other applications with optically pumped magnetometers. The present disclosure is also directed to the area of magnetic field measurement systems including systems for magnetoencephalography (MEG).

BACKGROUND

In the nervous system, neurons propagate signals via action potentials. These are brief electric currents which flow down the length of a neuron causing chemical transmitters to be released at a synapse. The time-varying electrical currents within an ensemble of neurons generate a magnetic field. Magnetoencephalography (MEG), the measurement of magnetic fields generated by the brain, is one method for observing these neural signals.

Existing systems for observing or measuring MEG typically utilize superconducting quantum interference devices (SQUIDs) or collections of discrete optically pumped magnetometers (OPMs). SQUIDs require cryogenic cooling which is bulky and expensive and requires a lot of maintenance which preclude their use in mobile or wearable devices. A challenge for OPM systems is maintaining a stable input light intensity into the vapor cell.

BRIEF SUMMARY

One embodiment is a magnetic field measurement system that includes a light source configured to emit a light beam; an optical fiber configured to transmit the light beam from the light source; a variable optical attenuator configured to receive the light beam from the optical fiber and to increase stability of an intensity of the light beam; a beam splitter configured to receive the light beam from the variable optical attenuator and divide the light beam into an OPM light beam and a monitor light beam; a monitor detector configured to receive and detect the monitor light beam and to generate a monitor signal; a vapor cell with alkali metal atoms disposed therein and configured for transmission of the OPM light beam through the vapor cell; an OPM detector configured to receive and detect the OPM light beam after transmission through the vapor cell and to generate an OPM signal; and a group delay filter configured to combine the monitor signal and the OPM signal to generate a reduced noise OPM signal, wherein the group delay filter is configured to account for a phase difference between the monitor signal and the OPM signal when combining the monitor signal and the OPM signal.

In at least some embodiments, the magnetic field measurement system further includes a first lock-in amplifier disposed between the OPM detector and the group delay filter and a second lock-in amplifier disposed between the monitor detector and the group delay filter. In at least some embodiments, the magnetic field measurement system further includes a demixer configured to demix the reduced noise OPM signal to provide a measurement of a magnetic field detected using the vapor cell.

In at least some embodiments, the magnetic field measurement system further includes a polarizer disposed between the variable optical attenuator and the beam splitter. In at least some embodiments, the polarizer includes a linear polarizer and a half wave plate.

In at least some embodiments, the magnetic field measurement system further includes a controller configured to receive the monitor signal and to adjust the variable optical attenuator based on the monitor signal. In at least some embodiments, the magnetic field measurement system further includes a collimating lens disposed between the variable optical attenuator and the beam splitter.

In at least some embodiments, the magnetic field measurement system further includes a reference vapor cell disposed between the beam splitter and monitor detector for transmission of the monitor light beam through the reference vapor cell.

In at least some embodiments, the group delay filter is configured to account for the phase difference between the monitor signal, M, and the OPM signal, A, according to the following equation:

$$A - \frac{\delta_a}{\delta_m} e^{i(\phi_a - \phi_m)} M = 0$$

wherein $\delta_a$ and $\delta_m$ are amplitudes of an optical noise term measured at the OPM detector and the monitor detector, respectively, and $\phi_a$ and $\phi_m$ are phases of the optical noise term measured at the OPM detector and the monitor detector, respectively. In at least some embodiments, $\phi_m = \arg[\tilde{M}(\omega_{opt} - \omega)]$, $\phi_a = \arg[\tilde{A}(\omega_{opt} - \omega)]$, $\delta_m = |\tilde{M}(\omega_{opt} - \omega)|$, and $\delta_m = |\tilde{A}(\omega_{opt} - \omega)|$, wherein $\tilde{M}$, $\tilde{A}$ are the Fourier transform of M, A, respectively, and $\omega_{opt}$ is an optical modulation tone applied to the light beam by the variable optical attenuator.

In at least some embodiments, the group delay filter includes a delay block configured to delay the monitor signal from the monitor detector to at least partially account for the phase difference between the monitor signal and the OPM signal. In at least some embodiments, the group delay filter further includes a MPD matrix configured to combine the delayed monitor signal and the OPM signal to generate the reduced noise OPM signal and the system further includes a lock-in amplifier configured to receive the reduced noise lock-in amplifier signal.

Another embodiment is a method for reducing optical noise in a magnetic field measurement system. The method includes emitting a light beam from a light source; stabilizing an intensity of the light beam using a variable optical attenuator; after stabilizing the intensity of the light beam, splitting the light beam into a monitor light beam and an OPM light beam; transmitting the OPM light beam through a vapor cell with alkali metal atoms disposed therein; after transmitting the OPM light beam through the vapor cell, detecting the OPM light beam using an OPM detector and generating an OPM signal; detecting the monitor light beam using a monitor detector and generating a monitor signal; and combining the monitor signal and the OPM signal using a group delay filter to generate a reduced noise OPM signal, where the group delay filter is configured to account for a phase difference between the monitor signal and the OPM signal when combining the monitor signal and the OPM signal.

In at least some embodiments, the method further includes demixing the reduced noise OPM signal to provide a measurement of a magnetic field detected using the vapor cell. In at least some embodiments, the method further includes adjusting the variable optical attenuator based on the monitor signal.

In at least some embodiments, combining the monitor signal and the OPM signal using a group delay filter includes accounting for the phase difference between the monitor signal, M, and the OPM signal, A, according to the following equation:

$$A - \frac{\delta_a}{\delta_m} e^{i(\phi_a - \phi_m)} M = 0$$

wherein $\delta_a$ and $\delta_m$ are amplitudes of an optical noise term measured at the OPM detector and the monitor detector, respectively, and $\phi_a$ and $\phi_m$ are phases of the optical noise term measured at the OPM detector and the monitor detector, respectively. In at least some embodiments, $\phi_m = \arg[\tilde{M}(\omega_{opt} - \omega)]$, $\phi_a = \arg[\tilde{A}(\omega_{opt} - \omega)]$, $\delta_m = |\tilde{M}(\omega_{opt} - \omega)|$, and $\delta_m = |\tilde{A}(\omega_{opt} - \omega)|$, wherein $\tilde{M}$, $\tilde{A}$ are the Fourier transform of M, A, respectively, and $\omega_{opt}$ is an optical modulation tone applied to the light beam by the variable optical attenuator.

In at least some embodiments, combining the monitor signal and the OPM signal using a group delay filter includes delaying, using a delay block, the monitor signal from the monitor detector to at least partially account for the phase difference between the monitor signal and the OPM signal.

In at least some embodiments, the method further includes transmitting the monitor light beam through a reference vapor cell prior to detecting the monitor light beam. In at least some embodiments, the method further includes polarizing the light beam prior to splitting the light beam.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
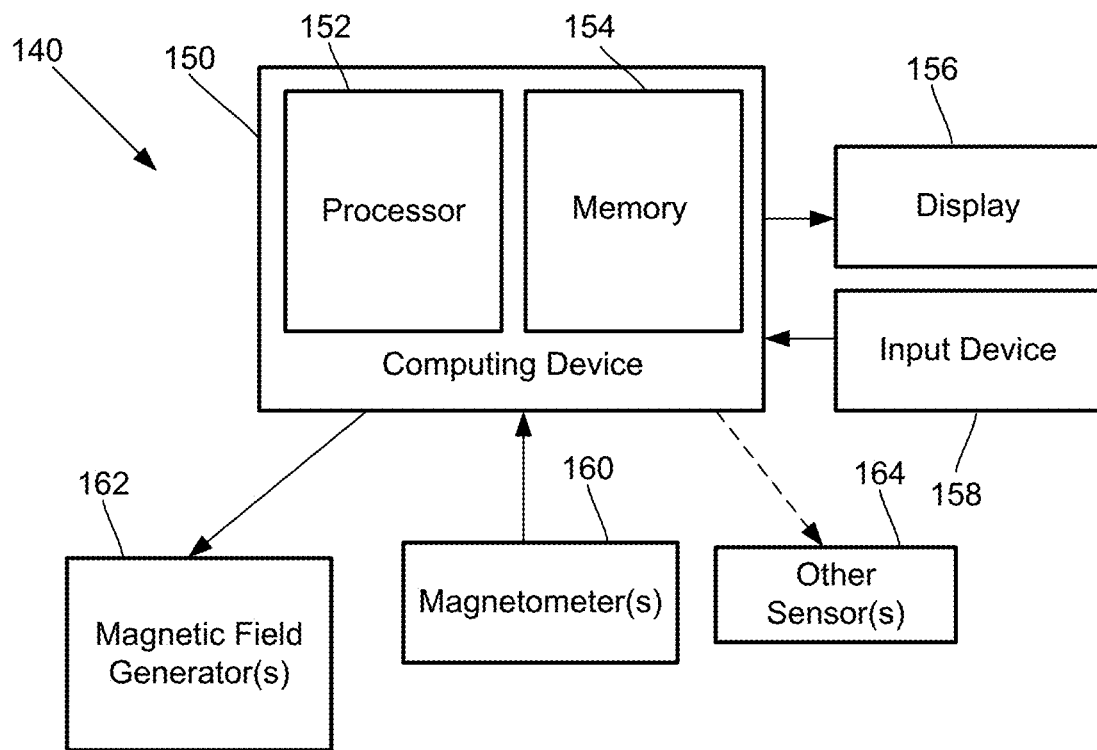
FIG. 1A is a schematic block diagram of one embodiment of a magnetic field measurement system, according to the invention.

The present disclosure is directed to magnetic field measurement systems and other applications with optically pumped magnetometers. The present disclosure is also directed to the area of magnetic field measurement systems including systems for magnetoencephalography (MEG).

Although the present disclosure utilizes magnetoencephalography (MEG) to exemplify the light intensity modulators, systems, and methods described herein, it will be understood that the light intensity modulators, systems, and methods can be used in any other suitable application.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's magnetic field.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. This technology can also be applicable for uses outside biomedical sensing.

In at least some embodiments, the system can be a wearable MEG system that can be used outside a magnetically shielded room. Examples of wearable MEG systems are described in U.S. Pat. No. 10,983,177 and U.S. Provisional Patent Applications Ser. Nos. 63/031,469; 63/076, 015; and 63/170,892, all of which are incorporated herein by reference in their entireties.

A magnetic field measurement system can utilize one or more magnetic field sensors. Magnetometers will be used herein as an example of magnetic field sensors, but other magnetic field sensors may also be used. FIG. 1A is a block diagram of components of one embodiment of a magnetic field measurement system 140. The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement systems, such as MEG systems, or methods of making such systems or components for such systems are described in Examples of magnetic field measurement systems in which the embodiments presented above can be incorporated, and which present features that can be incorporated in the embodiments presented herein, are described in U.S. Pat. Nos. 10,627,460; 10,976,386; 10,983,177; 10,996,293; 11,022,658; 11,131,729; 11,136,647; 11,237,225; 11,262,420; and 11,269,027; U.S. Patent Application Publications Nos. 2019/0391213; 2020/0109481; 2020/0123416; 2020/0191883; 2020/0241094; 2020/0309873; 2020/0334559; 2020/0381128; US 2021/0011094; 2021/0015385; 2021/0041512; 2021/0063510; 2021/0139742; 2021/0369165; 2021/0373092; 2021/0369201; and 2021/0369166; U.S. patent application Ser. No. 17/338,429; and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/052,327; 63/076,015; 63/076,880; 63/080,248; 63/089,456; 63/135,364; 63/136,093; 63/136,415; 63/140,150; 63/158,700; 63/159,823; 63/170,892; 63/189,870; 63/224,768; and 63/257,491, all of which are incorporated herein by reference in their entireties. The OPMs, OPM modules, and other system components described in these references can be used in the MEG and other magnetic field measurement systems and methods described herein.

Figure 1B:
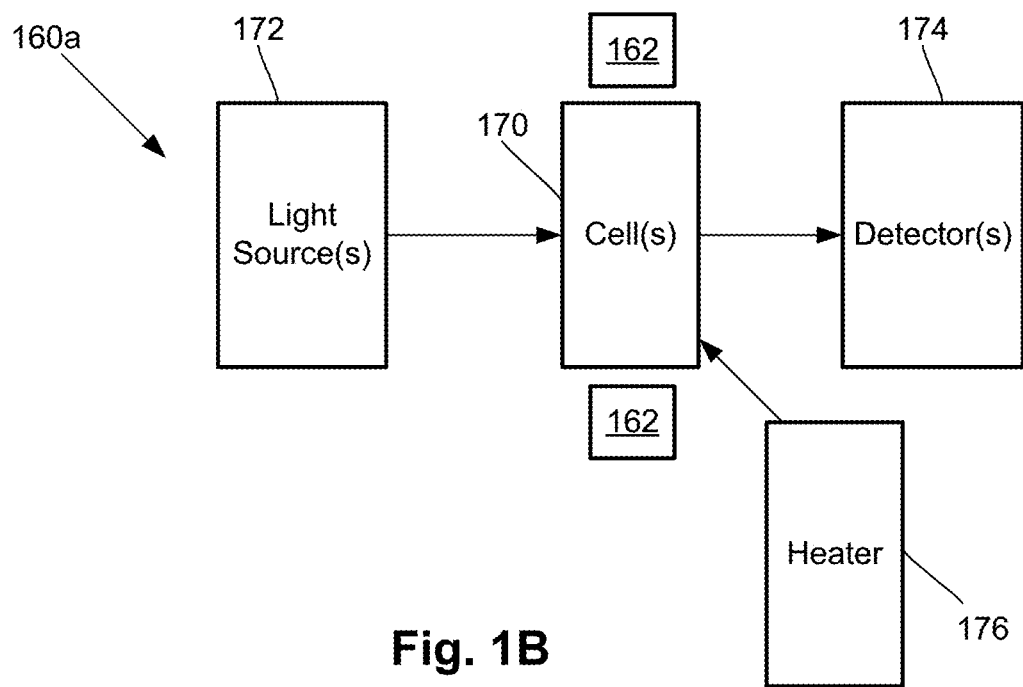
FIG. 1B is a schematic block diagram of one embodiment of a magnetometer, such as an OPM module, according to the invention.

FIG. 1B is a schematic block diagram of one embodiment of a magnetometer, such as an OPM module 160a, which includes one or more vapor cells 170 (also referred to as "cells") such as alkali metal vapor cells; a heating device 176 to heat the vapor cell(s) 170; one or more light sources 172 (which can include multiple different light sources, such as a pump light source and a probe light source); and one or more OPM detectors 174. In addition, coils of a magnetic field generator 162 can be positioned around the vapor cell(s) 170. The vapor cell(s) 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source(s) 172 can each include, for example, a laser to, respectively, optically pump the alkali metal atoms and probe the vapor cell. The light source(s) 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), distributed feedback laser (DFB)), external cavity diode laser (ECDL), light-emitting diode (LED), lamp, or any other suitable light source. In at least some embodiments, light can be delivered to the vapor cell via free-space optics or through a fiber optic arrangement with optical fibers or any combination thereof.

The OPM detector(s) 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable OPM detectors (or other detectors, such as the monitor detector describe below) include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
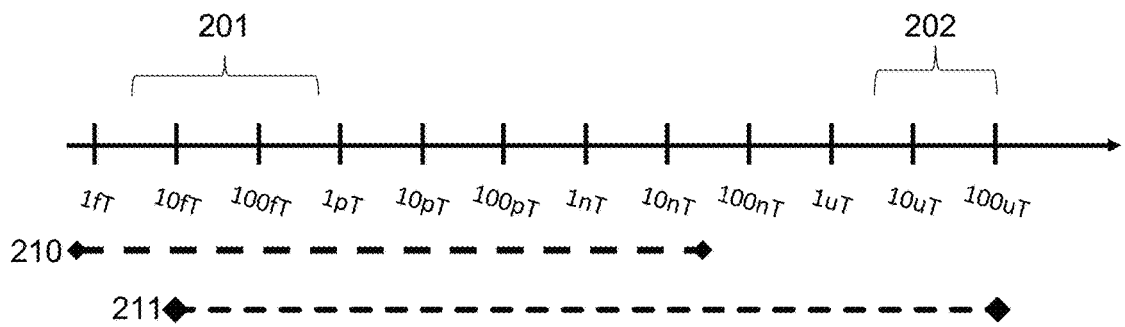
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 μT.

A challenge for OPM systems is maintaining a stable input light intensity into the vapor cell. Commercially available absorption-based SERF (spin-exchange relaxation-free) optically pumped magnetometers (OPMs) use VCSELs (vertical cavity side-emitting lasers) as low-noise and low-power light sources. The resulting narrow magnetic resonance lines can limit the operating range.

In contrast to these OPM systems, light sources, such as distributed feedback or distributed Bragg reflector lasers, with optical fiber delivery of light to the vapor cell can provide substantially higher power. In at least some embodiments, higher power can result in improved fundamental performance limits, particularly when the detection of photons is limited by shot noise of the OPM detector.

In practice, however, intensity fluctuations of the light source or arising in the fiber delivery arrangement can produce substantial detection noise. In at least some embodiments, a system can include a variable optical attenuator (VOA) to stabilize the light intensity. The VOA is positioned between the light source and the vapor cell. A VOA, however, also produces optical noise.

Methods, devices, and systems are described herein for suppression of optical noise in optical pumping magnetometers. In at least some embodiments, the methods, devices and system can achieve photon shot noise-limited sensitivity even with noisy input light. In at least some embodiments, methods, devices, and systems for removing optical noise in absorption based optically pumped magnetometers include measurement of optical noise at a point in the path before the vapor cell of the OPM using a monitor detector, such as a photodiode. The measured optical noise can be combined with the measured optical signal from the OPM detector, such as a photodiode, positioned after the vapor cell in order to reduce the optical noise in the optical signal.

In at least some embodiments, a filtering algorithm (which may be embodied as a group delay filter in software, hardware, or any combination thereof) is used to reduce optical noise in optically pumped magnetometers. In at least some embodiments, the filtering algorithm or group delay filter accounts for propagation delays due to propagation of resonant light through a medium (for example, a vapor containing alkali metal atoms) with a polarizable ground state. In at least some embodiments, in addition to group delays introduced by alkali metal atoms, the filtering algorithm or group delay filter can also be used to compensate for phase shifts introduced by any optical or electronic element in the monitor and vapor cell paths. In at least some embodiments, a calibration algorithm is used to determine or optimize the parameters of the group delay filter or filtering algorithm. In at least some embodiments, the methods, devices, and systems enable photon shot noise limited detection even with noisy input light intensity.

In at least some embodiments, the methods, devices, and systems have a dramatic reduction of noise in fiber-coupled, absorption-based magnetometers compared to the same method, device, or system without a group delay filter or filtering algorithm. In at least some embodiments, the methods, devices, and systems account for phase shifts that occur between signals and references, independent of source (atomic, analog electronics, or digital delays). In at least some embodiments, the methods, devices, and systems enable use of low cost, noisy variable optical attenuators (VOAs) without compromising sensitivity.

Figure 3:
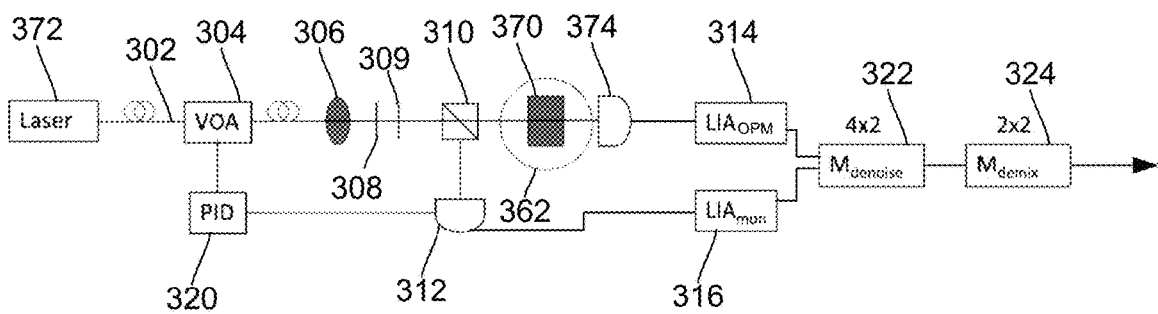
FIG. 3 shows a schematic illustration of one embodiment of magnetic measurement system with a variable optical attenuator and a group delay filter, according to the invention.

FIG. 3 illustrates one embodiment of elements of a magnetic field measurement system 300 and illustrating a signal processing chain for reduction of optical noise in an absorption-based atomic magnetometer, such as an OPM. Light from a light source 372, such as a laser, travels along an optical fiber 302 and passes through an inline variable optical attenuator (VOA) 304 and is collimated by a lens 306. Optical fibers can also be used to carry the light beam between any other components of the magnetic field measurement system. A linear polarizer 308 and a half wave plate 309 fixes the polarization of the light before the beam is divided into two paths by a beam splitter 310. A monitor light beam is directed to a monitor detector 312, such as a photodiode, and an OPM light beam is transmitted through a vapor cell 370 of an OPM and collected by an OPM detector 374, such as a photodiode. In response to the monitor light beam, the monitor detector 312 generates a monitor signal that is provided to a controller 320 (such as a proportional, integral, and derivative (PID) controller) for controlling the VOA 304 in a feedback loop. At least one magnetic field generator 362, such as a set of coils, is used to generate bias and modulation magnetic fields in the region of space around the vapor cell.

In at least some embodiments, the optical noise detected by the monitor detector 312 before the vapor cell 370 can be subtracted from the signal generated by the OPM detector 374 position after the vapor cell. To be most effective, the combination of signals generated by the monitor detector 312 and the OPM detector 374 accounts for the difference in phase for the two signals arising from, for example, the difference in paths of the monitor light beam and the OPM light beam. For example, the OPM light beam passes through the vapor cell 370 and can be delayed due to atomic transitions. In at least some embodiments, as described below, the phase difference between the signal from the monitor detector 312 and signal from the OPM detector 374 are taken into account to effectively reduce optical noise in the signal from the OPM detector. The phase difference can arise from the finite group velocity of light resonant with an atomic transition and other effects and differences in the light paths of the monitor light beam and the OPM light beam.

In at least some embodiments, signals from both the monitor detector 312 and the OPM detector 374 are analyzed by lock-in amplifiers 314, 316 using a magnetic modulation frequency (for example, in the range of 1-2 kHz). The signals are directed through a group delay filter 322 and a demixer 324. In at least some embodiments, the group delay filter 322 utilizes a 4×2 matrix as a linear operator to account for the phase difference between the two signals and to combine the two signals into a noise-reduced OPM detector signal. In at least some embodiments, the demixer utilizes a 2×2 matrix 324 to take the filtered quadratures of the noise-reduced OPM detector signal and interpret them as magnetic fields in an orthogonal basis (i.e., the demixer outputs the magnetic field measurement.)

Light that is resonant with an atomic transition, for example, the D1 transition of the alkali metal atoms in the vapor cell 370, optically pumps the ground state spins of the alkali metal atoms. As the atomic vapor becomes polarized along the pump beam, the transparency of the vapor cell 370 increases. The atomic spins precess about magnetic fields, resulting in reduced transparency of the vapor cell when there is a magnetic field transverse to the laser beam. The change in transparency of the atomic vapor cell with respect to magnetic field enables measurement of magnetic fields using, for example, the magnetic field measurement systems described above.

Noise in the input light beam compromises sensitivity. The measurement of noise in the light beam intensity before the light beam reaches the vapor cell 370 using the monitor detector 312 can facilitate suppression of noise at the OPM detector 374. However, additional suppression can be achieved by taking into account additional considerations as described below.

The impact of optical noise on the atomic spin polarization, in the presence of sufficient buffer gas pressure (for example, sufficient pressure to broaden the hyperfine spectra), can be approximated by the Bloch equations. For simplicity, at zero magnetic field:

$$dP_z/dt = \frac{1}{q}[R(1 - P_z) - \Gamma P_z], \qquad \text{(Eq. 1)}$$

where R is the optical pumping rate, $P_z$ is the atomic spin polarization along the light beam, $\Gamma$ is the spin destruction rate, and q is the nuclear slowing down factor which depends on both the nuclear spin I and the polarization P. For $^{87}$Rb with nuclear spin I=3/2, q=(2I+1)/(2−4/(3+P²)). The pump rate can have a DC term and a small sinusoidal term approximating noise:

$$R_{in}(t)=R_0+\delta_R \cos(\omega t). \quad \text{(Eq. 2)}$$

The solution to Equations (1) and (2) is $$P_z=P_0+\delta_P \cos(\omega t - \phi) \quad \text{(Eq. 3)}$$

where $$P_0 = \frac{R_0}{R_0+\Gamma}, \quad \text{(Eq. 4)}$$

$$\delta_P = \frac{\delta_R}{q}\sqrt{\frac{1}{\omega^2+\Delta\omega^2}}, \quad \text{(Eq. 5)}$$

$$\Delta\omega = (R_0+\Gamma)/q, \text{ and} \quad \text{(Eq. 6)}$$

$$\phi = \arctan(\omega/\Delta\omega). \quad \text{(Eq. 7)}$$

This analysis shows that the z component of polarization oscillates in response to a sinusoidal drive term with a phase shift $\phi$ with respect to the input sinusoidal perturbation.

The transmission of light through the vapor cell 370 can be described by Beer's law $$\frac{dR}{dz} = -n\sigma R(1-P_z). \quad \text{(Eq. 8)}$$

where, n is the atomic density, $\sigma$ is the absorption cross section, and z is the propagation length.

Because the transmitted light depends on the z component of polarization, the sinusoidal noise term at the output of the vapor cell 370 is phase shifted along with the z component of spin polarization. In the thin cell regime, where $P_z$ does not change much, the solution can be approximated by $$R=R_{in}e^{-n\sigma z(1-P_z)}.$$

Expanding this for small quantities in the exponent and including Equation 2, the pump rate at the output of the vapor cell 370 is approximately:

$$R_{out}=R_0[1-n\sigma z(1-P_0)]+\cos(\omega t)\delta_R(1-n\sigma z)+\cos(\omega t-\phi)(R_0 n\sigma z\delta_P). \quad \text{(Eq. 9)}$$

which can be rewritten as $$R_{out}=R_0[1-n\sigma z(1-P_0)]+A' \cos(\omega t-\phi') \quad \text{(Eq. 10)}$$

where $$A' = \sqrt{\delta_R^2(1-n\sigma z)^2+(R_0 n\sigma z\delta_P)^2\cos^2\phi}, \text{ and} \quad \text{(Eq. 11)}$$

$$\phi' = \frac{R_0 n\sigma z}{1-n\sigma z}\frac{1}{q}\frac{1}{\sqrt{\omega^2+\Delta\omega^2}}. \quad \text{(Eq. 12)}$$

These expressions are valid in the limit that the absorption length is small, $n\sigma z \ll 1$, and $\omega \gg \Delta\omega$ so that $\phi \approx \pi/2$. This approximation can break down in the limit of large optical depth $n\sigma z \geq 1$, but the general result of Equation 10 remains—the modulated component of the pump rate at the output of the vapor cell is shifted in phase with respect to the input.

Figure 4:
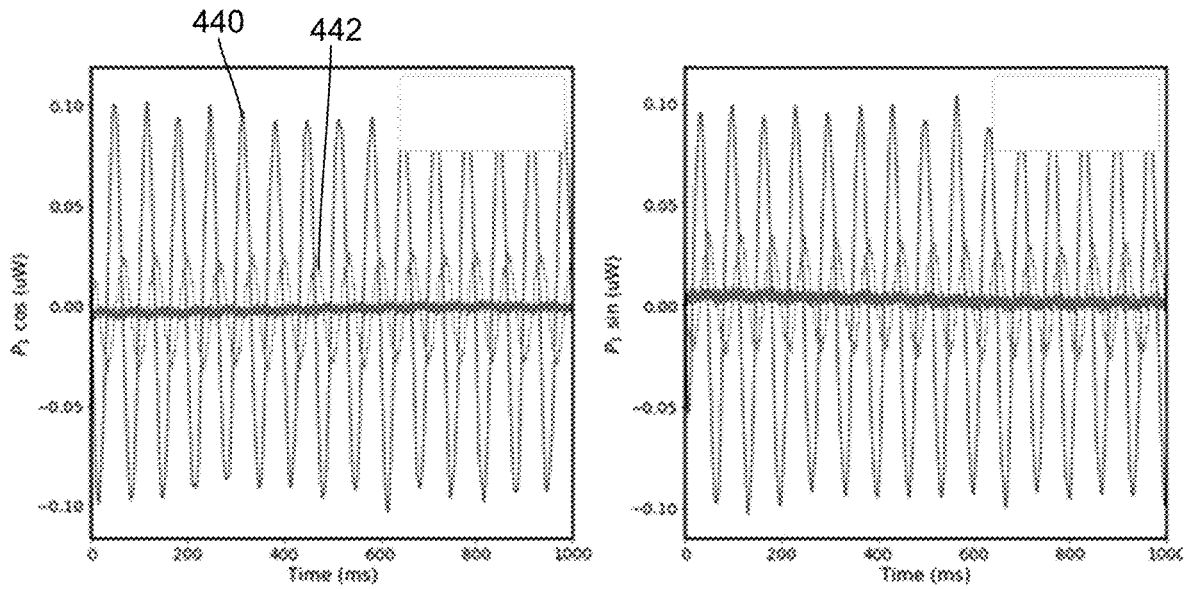
FIG. 4 is two graphs of polarization versus time for demodulated signals from the monitor detector and the OPM detector for experimental demonstration of atom-induced phase shift, according to the invention.

Experimental demonstration of the atom-induced phase shift is illustrated in FIG. 4 with the demodulated signal 440 from the monitor detector 312 and the demodulated signal 442 from the OPM detector 374 in the presence of a sinusoidal input power fluctuation. Trace 444 shows excellent suppression of the input power fluctuations via a group delay filter 322. The two panels show the demodulated quadratures of the monitor detector signal 440 and the OPM detector signal 442, as well as filter signal 444. There is a phase shift of approximately $\pi/2$ between the demodulated monitor detector signal 440 and the demodulated OPM detector signal 442.

Figure 5:
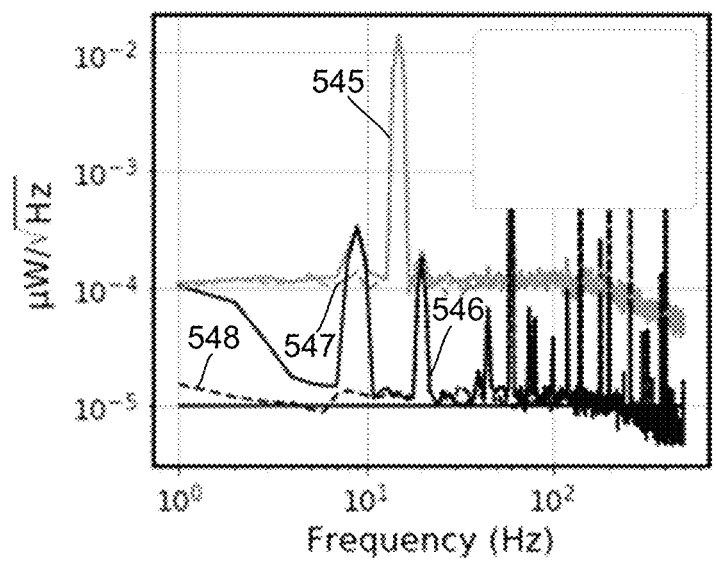
FIG. 5 is a graph of noise versus frequency for sine and cosine terms with and without application of a group delay filter, according to the invention.

Experimental validation of the group delay filter is provided in FIG. 5, with noise spectra for both quadratures before and after the group delay filter. FIG. 5 illustrates noise spectra of demodulated OPM detector signals before (signals 545 (cosine), 546 (sine)) and after (signal 547 (cosine), 548 (sine)) a group delay filter 322. The peak at 15 Hz is an optical calibration tone applied at 15 Hz away from the magnetic field modulation frequency and is suppressed by 30 dB using the group delay filter.

Methods, devices, and systems can compensate for the phase shift discussed above to substantially reduce noise in optical pumping magnetometers. The previous discussion described an atom-based phase shift, but there can also be other phase shifts, for example, phase shifts from analog electronics or digital signal processing. Adopting an agnostic approach to the source of the phase shifts, a sinusoidal optical noise term measured at the monitor detector 312 ($p_m$) and OPM detector 374 ($p_a$) can be parameterized as:

$$p_m=\delta_m \cos(\omega t+\phi_m) \text{ and} \quad \text{(Eq. 13)}$$

$$p_a=\delta_a \cos(\omega t+\phi_a), \quad \text{(Eq. 14)}$$

respectively. After demodulation with the lock-in amplifiers, the cosine and sine quadratures of the signal from the monitor detector 312 ($c_m$ and $s_m$) and the signal from the OPM detector 374 ($c_a$ and $s_a$) are:

$$c_m(t)=\delta_m(t)\cos(\phi_m), s_m(t)=\delta_m(t)\sin(\phi_m) \quad \text{(Eq. 15)}$$

$$c_a(t)=\delta_a(t)\cos(\phi_a), s_a(t)=\delta_a(t)\sin(\phi_a). \quad \text{(Eq. 16)}$$

The following linear combinations can be used:

$$M=\delta_m[\cos(\phi_m)+i\sin(\phi_m)]=\delta_m e^{i\phi_m} \quad \text{(Eq. 17)}$$

$$A=\delta_a[\cos(\phi_a)+i\sin(\phi_a)]=\delta_a e^{i\phi_a} \quad \text{(Eq. 18)}$$

These equations represent the complex optical noise in the monitor detector 312 (M) and the OPM detector (A), respectively. Noise in the OPM signal can be removed by subtracting an appropriately scaled and phased monitor signal, M, as follows:

$$\Delta = A - \frac{\delta_a}{\delta_m}e^{i(\phi_a-\phi_m)}M = 0 \quad \text{(Eq. 19)}$$

Equation 19 describes parameters for a group delay filter 322. The linear combination of OPM and monitor detector signals represented by Equation 19 can be accomplished using any suitable processing method or software/hardware. Such methods or software/hardware can include, but are not limited to, off-line processing using any suitable processing arrangement or real-time processing using a processing arrangement including a microprocessor or firmware running on an FPGA (field programmable gate array) or the like.

Equation 19 can be rewritten as a matrix equation that may be more convenient for real-time processing. A 1×4 signal vector includes the four quadratures of the OPM signal and the monitor signal $V = (A_c, A_s, M_c, M_s)$ A 4×2 matrix F represents the group delay filter $$F = \begin{pmatrix} 1 & 0 \\ 0 & 1 \\ \delta_a/\delta_m \cos(\phi_a - \phi_m) & \delta_a/\delta_m \sin(\phi_a - \phi_m) \\ -\delta_a/\delta_m \sin(\phi_a - \phi_m) & \delta_a/\delta_m \cos(\phi_a - \phi_m) \end{pmatrix}$$

The two denoised quadratures of the atom signal can be obtained from $\Delta = VF$ The parameters $\delta_a$, $\delta_m$, $\phi_a$, and $\phi_m$ of the group delay filter 322 can be determined using any suitable method include those described below. The parameters can be used for evaluating the filter performance.

One embodiment of a method for determining $\delta_a$, $\delta_m$, $\phi_a$, and $\phi_m$ includes application of an optical modulation tone $\omega_{opt}$ using the VOA 304. The lock-in amplifier reference frequency is denoted $\omega_{mod}$. The Fourier transform of the complex demodulated signals $\tilde{M}$, $\tilde{A}$ exhibits peaks at $\omega_{opt} - \omega_{mod}$ (see for example, the 15 Hz peak apparent in the unfiltered data shown in FIG. 5). Parameters for the filter can then be extracted:

$\phi_m = \arg[\tilde{M}(\omega_{opt} - \omega_{mod})]$ $\phi_a = \arg[\tilde{A}(\omega_{opt} - \omega_{mod})]$ $\delta_m = |\tilde{M}(\omega_{opt} - \omega_{mod})|$ $\delta_a = |\tilde{A}(\omega_{opt} - \omega_{mod})|$ Alternatively, instead of calculating the complete Fourier transform over all frequencies up to the Nyquist frequency, the Fourier amplitude can be calculated at a single frequency.

$A = A_c + iA_s, M = M_c + iM_s$ $R = e^{i(\omega_{opt} - \omega_{mod})t}$ $\delta_a = |\langle RA \rangle|$ $\delta_m = |\langle RM \rangle|$ $\phi_a = \arg(\langle AM \rangle)$ $\phi_m = \arg(\langle RM \rangle)$ Angled brackets indicate a time average over the calibration interval. R represents a reference signal against which the input signals are demodulated.

The relative amplitude of a calibration tone before and after the group delay filter provides a measure of the gain of the filter.

Figure 6:
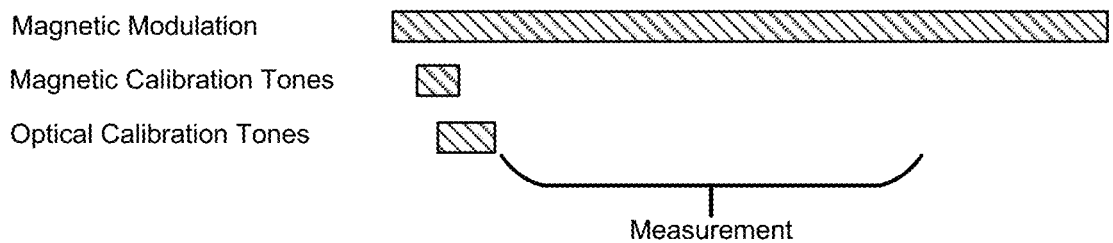
FIG. 6 illustrates one embodiment of a timing sequence for magnetic modulation using the magnetic field generator(s), as well as the application of magnetic calibration tones and optical calibration tones for the group delay filter, according to the invention.
Figure 7:
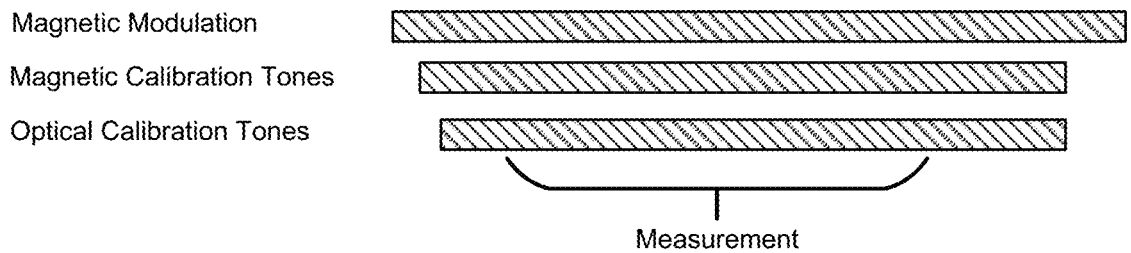
FIG. 7 illustrates another embodiment of a timing sequence for magnetic modulation using the magnetic field generator(s), as well as the application of magnetic calibration tones and optical calibration tones for the group delay filter, according to the invention.

One embodiment of a procedure to enable noise suppression in absorption-based magnetometers has a timing sequence, illustrated in FIG. 6, for magnetic modulation using the magnetic field generator(s) 162, as well as the application of magnetic calibration tones and optical calibration tones for the group delay filter 322. During calibration and magnetic field measurement, the magnetic field modulation using the magnetic field generator(s) 362 is always present. FIG. 7 illustrates another embodiment of a sequence of magnetic modulation, magnetic calibration tones, and optical calibration tones for the group delay filter 322. The magnetic and optical calibration tones are applied either sequentially (with no overlap), partially overlapping (FIGS. 6 and 7), or fully overlapping. In at least some embodiments, magnetic and optical calibration tones can also be applied throughout the measurement interval if there is concern that the calibration or scale factors drift with time.

Figure 8:
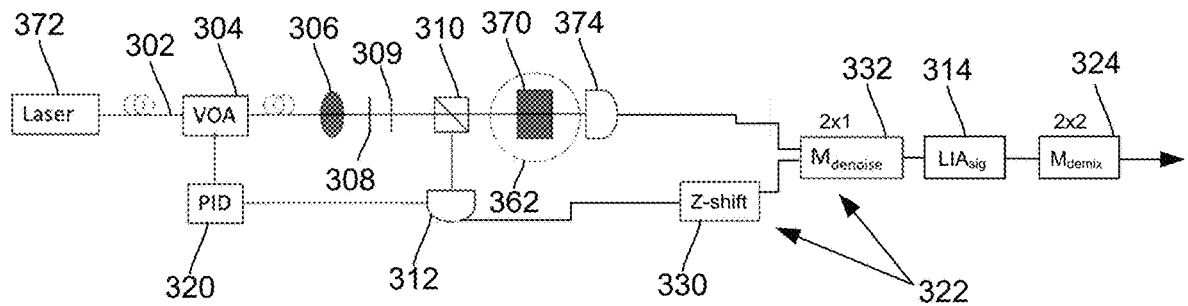
FIG. 8 is a schematic illustration of a second embodiment of magnetic measurement system with a variable optical attenuator and a group delay filter, according to the invention.

As described above, the relative phase and amplitude of the four demodulated quadratures can be adjusted to minimize or reduce noise. In other embodiments, phase shifts between the monitor detector signal and the OPM detector signal can be adjusted to minimize or reduce noise at the input to a lock-in amplifier. FIG. 8 illustrates one embodiment of a group delay filter using a z-shift delay in a signal path after the monitor detector 312 before demodulation via a lock-in amplifier 314. This can be accomplished via digital signal processing by a delay block 330 between the monitor detector 312 and a 2×1 matrix ($M_{denoise}$) 332 that scales the signals from the monitor detector 312 and the OPM detector 374 for combination. In a basis where the first and second elements correspond to the OPM and monitor detector signals, respectively, the entries of the 2×1 denoising matrix are $$M_{denoise} = \begin{pmatrix} 1 \\ -\delta_a/\delta_m \end{pmatrix}.$$

Figure 9:
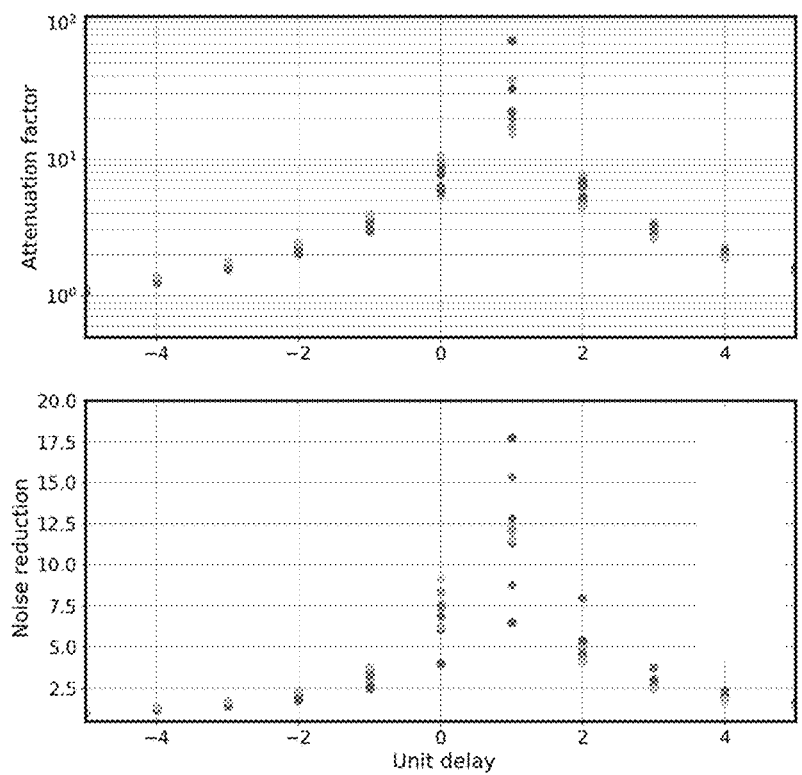
FIG. 9 is a graph of attenuation factor versus unit delay for experimental demonstration of a z-shift implementation of a group delay filter, according to the invention.

FIG. 9 illustrates experimental demonstration of the z-shift implementation of the group delay filter. The high bandwidth monitor data (before demodulation via the lock-in amplifier) is shifted before subtraction. In this case, attenuation of the optical calibration tone and the noise is optimized for a z-shift of 1 which corresponds to a 20 μs delay.

Figure 10:
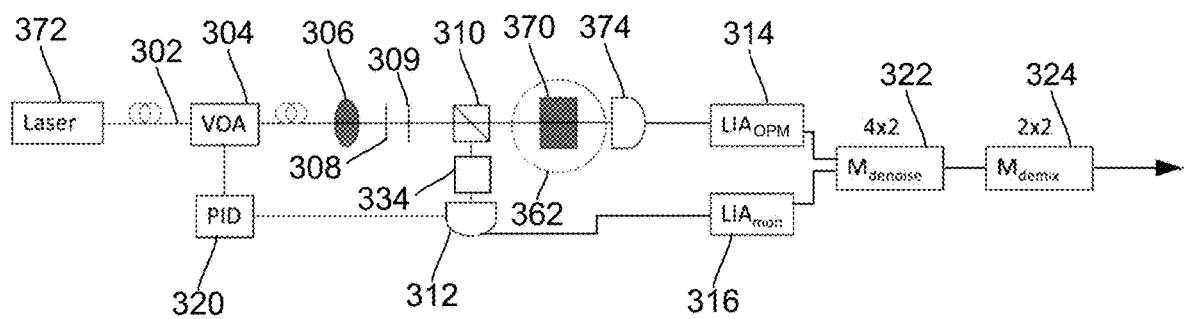
FIG. 10 is a schematic illustration of a third embodiment of magnetic measurement system with a variable optical attenuator and a group delay filter, according to the invention.

In another embodiment, as illustrated in FIG. 10, the light beam directed from the beam splitter 310 to the monitor detector 312 passes through a reference vapor cell 334 of similar characteristics as the vapor cell 370 before impinging on the monitor detector 312. In this embodiment, this light beam experiences a similar group delay as the light beam impinging on OPM detector 374 which may reduce the phase difference between the signal from the monitor detector 312 and the OPM detector 374. In at least some embodiments, there is no magnetic field generator 362 around the reference vapor cell 334.

In at least some embodiments, modulation of the optical intensity is used to provide a calibration tone to extract filter parameters. As described above, modulation can be applied via a variable optical attenuator. Other methods to generate optical modulations can also be used. For example, in another embodiment, the light from the light source 372 is transmitted directly to the vapor cell 370 without passing through a variable optical attenuator 304. The optical calibration tones are then applied by modulation of the light source such as, for example, modulation of the injection current of the diode laser.

As described above, in at least some embodiments, the group delay filter can be used to reduce optical noise in a magnetic field measurement system with optically pumped magnetometers (OPMs). Such magnetic field measurement systems can be used as, for example, magnetoencephalography (MEG) systems. Examples of magnetic field measurement or recording systems in which the embodiments described herein can be incorporated are described in Examples of magnetic field measurement systems in which the embodiments presented above can be incorporated, and which present features that can be incorporated in the embodiments presented herein, are described in U.S. Pat. Nos. 10,627,460; 10,976,386; 10,983,177; 10,996,293;

11,022,658; 11,131,729; 11,136,647; 11,237,225; 11,262,420; and 11,269,027; U.S. Patent Application Publications Nos. 2019/0391213; 2020/0109481; 2020/0123416; 2020/0191883; 2020/0241094; 2020/0309873; 2020/0334559; 2020/0381128; US 2021/0011094; 2021/0015385; 2021/0041512; 2021/0063510; 2021/0139742; 2021/0369165; 2021/0373092; 2021/0369201; and 2021/0369166; U.S. patent application Ser. No. 17/338,429; and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/052,327; 63/076,015; 63/076,880; 63/080,248; 63/089,456; 63/135,364; 63/136,093; 63/136,415; 63/140,150; 63/158,700; 63/159,823; 63/170,892; 63/189,870; 63/224,768; and 63/257,491, all of which are incorporated herein by reference in their entireties.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A magnetic field measurement system, comprising:
a light source configured to emit a light beam;
an optical fiber configured to transmit the light beam from the light source;
a variable optical attenuator configured to receive the light beam from the optical fiber and to increase stability of an intensity of the light beam;
a beam splitter configured to receive the light beam from the variable optical attenuator and divide the light beam into an OPM light beam and a monitor light beam;
a monitor detector configured to receive and detect the monitor light beam and to generate a monitor signal;
a vapor cell with alkali metal atoms disposed therein and configured for transmission of the OPM light beam through the vapor cell;
an OPM detector configured to receive and detect the OPM light beam after transmission through the vapor cell and to generate an OPM signal; and
a group delay filter configured to combine the monitor signal and the OPM signal to generate a reduced noise OPM signal, wherein the group delay filter is configured to account for a phase difference between the monitor signal and the OPM signal when combining the monitor signal and the OPM signal.

2. A method for reducing optical noise in a magnetic field measurement system, the method comprising:
emitting a light beam from a light source;
stabilizing an intensity of the light beam using a variable optical attenuator;
after stabilizing the intensity of the light beam, splitting the light beam into a monitor light beam and an OPM light beam;
transmitting the OPM light beam through a vapor cell with alkali metal atoms disposed therein;
after transmitting the OPM light beam through the vapor cell, detecting the OPM light beam using an OPM detector and generating an OPM signal;
detecting the monitor light beam using a monitor detector and generating a monitor signal; and
combining the monitor signal and the OPM signal using a group delay filter to generate a reduced noise OPM signal, where the group delay filter is configured to account for a phase difference between the monitor signal and the OPM signal when combining the monitor signal and the OPM signal.

3. The magnetic field measurement system of claim 1, further comprising a first lock-in amplifier disposed between the OPM detector and the group delay filter and a second lock-in amplifier disposed between the monitor detector and the group delay filter.

4. The magnetic field measurement system of claim 1, further comprising a demixer configured to demix the reduced noise OPM signal to provide a measurement of a magnetic field detected using the vapor cell.

5. The magnetic field measurement system of claim 1, further comprising a polarizer disposed between the variable optical attenuator and the beam splitter.

6. The magnetic field measurement system of claim 5, wherein the polarizer comprises a linear polarizer and a half wave plate.

7. The magnetic field measurement system of claim 1, further comprising a controller configured to receive the monitor signal and to adjust the variable optical attenuator based on the monitor signal.

8. The magnetic field measurement system of claim 1, further comprising a collimating lens disposed between the variable optical attenuator and the beam splitter.

9. The magnetic field measurement system of claim 1, further comprising a reference vapor cell disposed between the beam splitter and monitor detector for transmission of the monitor light beam through the reference vapor cell.

10. The magnetic field measurement system of claim 1, wherein the group delay filter is configured to account for the phase difference between the monitor signal, M, and the OPM signal, A, according to the following equation:

$$A - \frac{\delta_a}{\delta_m} e^{i(\phi_a - \phi_m)} M = 0$$

wherein $\delta_a$ and $\delta_m$ are amplitudes of an optical noise term measured at the OPM detector and the monitor detector, respectively, and $\phi_a$ and $\phi_m$ are phases of the optical noise term measured at the OPM detector and the monitor detector, respectively.

11. The magnetic field measurement system of claim 10, wherein $\phi_m = \arg[\tilde{M}(\omega_{opt} - \omega)]$, $\phi_a = \arg[\tilde{A}(\omega_{opt} - \omega)]$, $\delta_m = |\tilde{M}(\omega_{opt} - \omega)|$, and $\delta_m = |\tilde{A}(\omega_{opt} - \omega)|$, wherein $\tilde{M}$, $\tilde{A}$ are the Fourier transform of M, A, respectively, and $\omega_{opt}$ is an optical modulation tone applied to the light beam by the variable optical attenuator.

12. The magnetic field measurement system of claim 1, wherein the group delay filter comprises a delay block configured to delay the monitor signal from the monitor detector to at least partially account for the phase difference between the monitor signal and the OPM signal.

13. The magnetic field measurement system of claim 12, wherein the group delay filter further comprises a MPD matrix configured to combine the delayed monitor signal and the OPM signal to generate the reduced noise OPM signal and the magnetic field measurement system further comprises a lock-in amplifier configured to receive the reduced noise OPM signal.

14. The method of claim 2, further comprising demixing the reduced noise OPM signal to provide a measurement of a magnetic field detected using the vapor cell.

15. The method of claim 2, further comprising adjusting the variable optical attenuator based on the monitor signal.

16. The method of claim 2, wherein combining the monitor signal and the OPM signal using a group delay filter comprises accounting for the phase difference between the monitor signal, M, and the OPM signal, A, according to the following equation:

$$A - \frac{\delta_a}{\delta_m} e^{i(\phi_a - \phi_m)} M = 0$$

wherein $\delta_a$ and $\delta_m$ are amplitudes of an optical noise term measured at the OPM detector and the monitor detector, respectively, and $\phi_a$ and $\phi_m$ are phases of the optical noise term measured at the OPM detector and the monitor detector, respectively.

17. The method of claim 16, wherein $\phi_m = \arg[\tilde{M}(\omega_{opt} - \omega)]$, $\phi_a = \arg[\tilde{A}(\omega_{opt} - \omega)]$, $\delta_m = |\tilde{M}(\omega_{opt} - \omega)|$, and $\delta_m = |\tilde{A}(\omega_{opt} - \omega)|$, wherein $\tilde{M}$, $\tilde{A}$ are the Fourier transform of M, A, respectively, and $\omega_{opt}$ is an optical modulation tone applied to the light beam by the variable optical attenuator.

18. The method of claim 2, wherein combining the monitor signal and the OPM signal using a group delay filter comprises delaying, using a delay block, the monitor signal from the monitor detector to at least partially account for the phase difference between the monitor signal and the OPM signal.

19. The method of claim 2, further comprising transmitting the monitor light beam through a reference vapor cell prior to detecting the monitor light beam.

20. The method of claim 2, further comprising polarizing the light beam prior to splitting the light beam.

* * * * *